United States Patent [19]

Maki et al.

[11] Patent Number: 4,649,217

[45] Date of Patent: Mar. 10, 1987

[54] PROCESS FOR PRODUCING OXOCARBOXYLIC ACIDS

[75] Inventors: Takao Maki, Fujisawa; Kenji Murayama, Yokohama; Yoshio Asahi, Sagamihara, all of Japan

[73] Assignee: Mitsubishi Chemical Industries Limited, Tokyo, Japan

[21] Appl. No.: 475,646

[22] Filed: Mar. 15, 1983

[30] Foreign Application Priority Data

| Apr. 2, 1982 | [JP] | Japan | 57-53908 |
| May 24, 1982 | [JP] | Japan | 57-87607 |
| Jul. 21, 1982 | [JP] | Japan | 57-127054 |
| Sep. 2, 1982 | [JP] | Japan | 57-153069 |

[51] Int. Cl.$^4$ .............. C07C 51/31; C07C 59/147; C07C 59/185
[52] U.S. Cl. ........................... 562/528; 562/577; 260/413
[58] Field of Search ............. 562/577, 528; 260/413

[56] References Cited

U.S. PATENT DOCUMENTS

| 2,316,543 | 4/1943 | Amend | 562/528 |
| 3,419,605 | 12/1968 | Mead | 562/528 |
| 3,780,098 | 12/1973 | Morris | 562/528 |

FOREIGN PATENT DOCUMENTS 26768 7/1972 Japan.
181039 11/1982 Japan.

*Primary Examiner*—Werren B. Lone
*Attorney, Agent, or Firm*—Oblon, Fisher, Spivak, McClelland & Maier

[57] ABSTRACT

Oxocarboxylic acids, for example adipaldehydic acid can be advantageously produced by a process, in which cyclohexanones are oxidized with molecular oxygen in the presence of water and iron or iridium compound, preferably also in the presence of a sulfur or organic nitrogen compound.

21 Claims, No Drawings

PROCESS FOR PRODUCING OXOCARBOXYLIC ACIDS

BACKGROUND OF THE INVENTION

Adipaldehydic acid is a useful compound as a synthetic intermediate. Some processes of producing the acid have already been known. In one process, 2-hydroxycyclohexanone is oxidized with lead tetraacetate. In another process, cyclohexanone is oxidized at a low temperature with alkaline hydrogen peroxide. However, these processes are not so advantageous, because they need expensive chemicals and are of poor yield.

Recently, it was reported that adipaldehydic acid methyl ester and dimethyl acetal thereof are produced by oxidizing cyclohexanone with molecular oxygen in methanol in the presence of ferric chloride. However, the reaction rate is too slow in this process. Besides, the process is practically disadvantageous because a complicated operation to remove the methoxy group is inevitable in order to use the resulting product, which has a methoxy group derived from methanol, as a synthetic intermediate.

In another example, it was reported that adipaldehydic acid can be produced by oxidizing cyclohexanone with molecular oxygen in the presence of water and a copper compound (Japanese Patent Publication No. 26768/1972). However, the process of the patent is disadvantageous because the conversion of cyclohexanone and the yield of the desirable product are both not sufficiently high. And also, the reaction rate is not fast enough to conduct the reaction within an advantageously short time.

SUMMARY OF THE INVENTION

The inventors of the present invention have earnestly studied and have now found that free adipaldehydic acid can be produced in a good yield in high reaction rate by oxidizing a mixture of water and cyclohexanone with molecular oxygen in the presence of an iron or iridium compound and reached the present invention.

And also, we have found that a remarkably good result can be obtained by using an iron or iridium compound together with a sulfur compound or an organic nitrogen compound.

BRIEF DESCRIPTION OF THE INVENTION

In the present invention, cyclohexanones represented by the following formula (I)

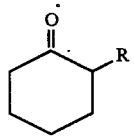
(I)

are oxidized with molecular oxygen in the presence of (1) water, (2) an iron or iridium compound, preferably also in the presence of a sulfur or organic nitrogen compound to produce oxocarboxylic acids represented by the following formula (II)

RCO(CH$_2$)$_4$COOH     (II)

R in the formula (I) and (II) has the same meaning, which means hydrogen or an alkyl group. The alkyl group is not limited, but an alkyl group having 6 or lower carbon atom is practically preferred.

The presence of water in the reaction is essential in order to conduct the present invention.

Water is used in an amount of from 0.05 to 1,000, preferably from 0.1 to 100 part by weight per part of cyclohexanone.

The reaction is conducted in a liquid phase. The state of the liquid phase will be a homogeneous or suspended state according to the mixing ratio of water. Either of the states can be adopted in the process of the present invention.

A solvent can be used in the oxidation in order to improve the homogeneity of the reaction system.

As such solvent, a non-protonic polar solvent such as dioxane or tetrahydrofuran may be used.

The temperature in the oxidation can be in the range of from 0° to 200° C., preferably from 30° to 90° C.

The oxidation proceeds in sufficient rate under atmospheric pressure, but a higher pressure can also be adopted.

Molecular oxygen can be supplied as pure oxygen or a diluted state such as air.

The one-pass conversion of cyclohexanones can be voluntarily chosen.

However, a good selectivity of oxocarboxylic acid can be obtained by controlling the conversion to less than 50%, because the higher conversion leads to an increase in the production of excessively oxidized products.

Iron or iridium compound applied for the present invention is preferably water-soluble compound.

They can be a salt of an inorganic acid such as ferrous chloride, ferric chloride, ferric bromide, ferrous sulfate, ferric nitrate or a salt of an organic acid such as ferrous acetate.

The amount of iron or iridium compound used can be widely changed, but it is preferable to use from 0.1 to 100, especially from 1 to 30% by mole (as iron or iridium) of cyclohexanone.

A remarkably good result can be obtained by using iron or iridium compound together with a sulfur or organic nitrogen compound.

A combination of an iron compound and a sulfur compound is especially preferred. Ferric chloride or nitrate and thiourea can be used.

Sulfur compounds can be a compound represented by the formulas of R—SH, R—S—R', R—S—S—R',

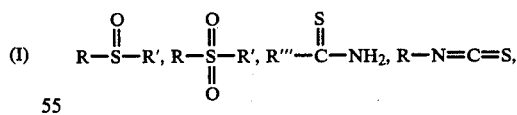

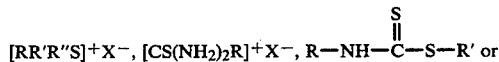

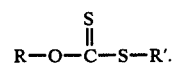

In the formulas R, R' or R'' is an alkyl or aryl group; R''' is an alkyl, aryl or unsubstituted or substituted amino groups; the alkyl or aryl group has 1–20, preferably 1–6 carbon atoms and may have substituents such as hydroxyl or amino group; X$^-$ represents anion. Sulfur compound can also be a saturated or unsaturated heterocyclic sulfur compounds or an inorganic sulfur compound.

These sulfur compounds are exemplified as follows.

R—SH: methyl mercaptan, ethylmercaptan, n-propylmercaptan, tert-butylmercaptan, 2-ethylhexylmercaptan, dodecylmercaptan, octadecylmercaptan, 2-hydroxyethylmercaptan, 2-aminoethylmercaptan, 2-mercaptoethane sulfonic acid, cyclopentylmercaptan, cyclohexylmercaptan, thiophenol, 4-nitrothiophenol, 4-(trifluoromethyl)thiophenol, 4-methylthiophenol, 2-mercaptopyridine, 4-mercaptopyridine, 2-(2-mercaptoethyl)pyridine, thioglycollic acid, 2-mercaptopropionic acid.

R—S—R': dimethyl sulfide, diethyl sulfide, di-(n-butyl)sulfide, di-(n-pentyl)sulfide, didodecyl sulfide, methionine, dicyclohexyl sulfide, diphenyl sulfide, 2-(2-thienyl)pyridine, thianaphthene, thiophene, 1,3-dithian, tetrahydrothiophene.

R—S—S—R': dimethyl disulfide, diethyl disulfide, diphenyl disulfide, cystine, 2,2-bipyridyl disulfide.

dimethyl sulfoxide, diphenyl sulfoxide.

dimethyl sulfone, dibutyl sulfone, diphenyl sulfone, butadiene sulfone.

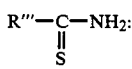

thioacetamide, thiopropionicamide, thiobenzamide, ω-thiocaprolactam, thionicotineamide, thiourea.

R—N=C=S: methylisothiocyanate.
[RR'R"S]+X−: trimethylsulfonium chloride
[CS(NH₂)₂R]³⁰X−: n-butylthiuronium chloride.

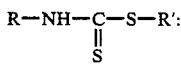

dithiocarbamic acid compound.

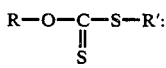

xanthogenic acid compound.

A saturated or unsaturated heterocyclic sulfur compound: 2-amino-2-thiazoline, thiazolidine, thioproline, benzothiazole, 2-aminobenzothiazole, 2-mercaptobenzothiazole, thiazole, 2-aminothiazolidine, 1,3-propanesultone, ethylene trithiocarbonate, phenothiazine, 4-amino-2-mercaptopyridine.

The amount of sulfur compound used is in the range of 0.1 to 100% by mole, preferably from 5 to 100% by mole (as sulfur) of iron or iridium.

Organic nitrogen compounds are exemplified as follows.

Amines: especially a tertiary amine such as triethylamine, trioctylamine, 1,4-diazabicyclo[2,2,2]octane.

Nitrogen containing heterocyclic compounds: pyridine, 4-pycoline, quinoline.

Oximes: especially glyoximes such as dimethylglyoxime, 1,2-cyclohexanedione.dioxime.

Hydroxamic acid: acetohydroxamic acid.

Amides: dimethylformamide, N-methylpyrrolidone and urea.

The amount of organic nitrogen compound used is in the range of 0.1 to 600% by mole, preferably from 10 to 300% by mole (as nitrogen) of iron or iridium.

Examples of the present invention are shown below, but the invention is not limited by the following examples.

EXAMPLE 1

The mixture of 1 g (10.2 m mol) of cyclohexanone, 9 g of water and 0.165 g (1.02 m mol) of anhydrous ferric chloride as catalyst was charged into a glass reactor and heated at 60° C.

Oxidation was conducted in an atmosphere of pure oxygen gas stream under strong oxidation.

After an hour from the start of the reaction, the pure oxygen stream was stopped to cease the reaction.

Resulting reaction mixture was subjected to esterification treatment in which the mixture was refluxed with methanol in an atmosphere of nitrogen gas stream in the presence of boron trifuluoride. The product was analyzed by gas chromatography. The conversion of cyclohexanone was 23.3% and the selectivity of adipaldehydic acid was 67.6%.

EXAMPLE 2 TO 5

Those examples were conducted in the same manner as in the Example 1 except that the following same reaction conditions were employed, Cyclohexanone—1 g (10.2 m mol),
Water—9 g,
Catalyst—1.02 m mol,
Temperature—60° C.,
Pressure—atmospheric,
Oxygen—pure oxygen.

and the catalyst and the reaction time shown in the Table 1 were adopted in each example.

TABLE I

| Ex. | Catalyst | Reaction time [min.] | Conversion of cyclohexanone [%] | Selectivity of adipaldehydic acid [%] |
|---|---|---|---|---|
| 2 | FeSO₄.7H₂O | 120 | 3.5 | 60.9 |
| 3 | Fe(NO₃)₃.9H₂O | 50 | 11.3 | 46.8 |
| 4 | FeBr₃ (anhydrous) | 60 | 18.6 | 77.8 |
| 5 | IrCl₄.H₂O | 60 | 25.0 | 39.4 |

EXAMPLE 6

The mixture of 0.1 g (1.02 m mol) of cyclohexanone, 9 g of water and 0.0165 g (0.102 m mol) of anhydrous ferric chloride as catalyst was heated at 60° C. Oxidation was conducted in an atmosphere of pure oxygen gas stream for 50 minutes. The conversion of cyclohexanone was 16.1% and the selectivity of adipaldehydic acid was 66.5%.

EXAMPLE 7

The mixture of 7.5 g (76.4 m mol) of cyclohexanone, 2.5 g of water and 1.24 g (7.6 m mol) of anhydrous ferric chloride as catalyst was heated at 60° C. Oxidation was conducted in an atmosphere of pure oxygen gas stream for 70 minutes. The conversion of cyclohexanone was 2.2% and the selectivity of adipaldehydic acid was 55.7%.

EXAMPLE 8 TO 26

The mixture of 1 g (10.2 m mol) of cyclohexanone, 10.6 g of water, 0.165 g (1.02 m mol) of anhydrous ferric chloride and the organic sulfur compounds shown in the Table II as catalyst was heated at 60° C. and atmospheric pure oxygen gas was introduced in the mixture under strong agitation.

The reaction was stopped after 2 m mol of oxygen was absorbed in the mixture. The product was analyzed by gas chromatography. Results are shown in the Table II.

drous ferric bromide 0.30 g (1.02 m mol) instead of anhydrous ferric chloride. Results are as follows.
Reaction time [min.]—75,
Conversion of cyclohexanone [%]—20.6,
Selectivity of adipaldehydic acid [%]—84.9.

EXAMPLE 37

In this example, the oxidation was conducted in the same manner as in the Example 8 except that following reaction mixture was employed,
2-methylcyclohexanone—1 g (8.91 m mol),
water—10.3 g,
anhydrous ferric chloride—0.144 g (0.89 m mol),
thiourea—0.034 g (0.45 m mol).
Results are as follows.
Reaction Time [min.]—150,
Conversion of 2-methylcyclohexanone [%]—27.8,

TABLE II

| Example No. | Organic sulfur compound | (m mol) | Reaction Time (min.) | Conversion of cyclohexanone [%] | Selectivity of adipaldehydic acid [%] |
|---|---|---|---|---|---|
| 8 | 2-mercaptopyridine | 0.51 | 65 | 24.8 | 84.8 |
| 9 | 2-mercaptopyridine | 0.01 | 60 | 26.4 | 73.6 |
| 10 | 4-mercaptopyridine | 0.50 | 75 | 23.4 | 85.1 |
| 11 | thiophenol | 0.54 | 65 | 23.7 | 80.5 |
| 12 | 4-nitrothiophenol | 0.50 | 60 | 26.2 | 74.8 |
| 13 | 2-mercaptoethanol | 0.67 | 75 | 24.0 | 85.0 |
| 14 | 2-mercaptoethylamine hydrochlorate | 0.45 | 60 | 23.9 | 82.8 |
| 15 | L-cysteine hydrochlorate | 0.51 | 65 | 24.4 | 84.3 |
| 16 | diethyl sulfide | 0.52 | 60 | 26.8 | 74.9 |
| 17 | diphenyl sulfide | 0.49 | 60 | 25.2 | 75.9 |
| 18 | dimethyl sulfoxide | 0.57 | 55 | 27.5 | 70.5 |
| 19 | thiourea | 0.49 | 70 | 22.4 | 89.4 |
| 20 | thioacetamide | 0.51 | 95 | 21.2 | 86.5 |
| 21 | thiazolidine | 0.55 | 70 | 27.6 | 78.0 |
| 22 | L-methionine | 0.47 | 65 | 27.2 | 79.3 |
| 23 | elemental sulfur | 0.54 | 60 | 26.7 | 73.4 |
| 24 | thiazole | 0.52 | 95 | 22.6 | 73.8 |
| 25 | phenothiazine | 0.49 | 125 | 26.6 | 70.8 |
| 26 | ethylene trithiocarbonate | 0.51 | 180 | 21.6 | 74.0 |

EXAMPLES 27 TO 35

In these examples, the oxidation was conducted in the same manner as in the Example 8 to 26 except using dioxane-water mixture (8:5 (weight ratio)) as solvent instead of water. Results are shown in the Table III.

Selectivity of 6-ketoheptanoic acid [%]—77.8.

EXAMPLE 38 TO 42

In these examples, the oxidation was conducted in the same manner as in the example 8 to 26 except using the inorganic sulfur compounds in the Table IV.

TABLE III

| Example No. | Organic sulfur compound | (m mol) | Reaction Time (min.) | Conversion of cyclohexanone [%] | Selectivity of adipaldehydic acid [%] |
|---|---|---|---|---|---|
| 27 | 2-mercaptopyridine | 0.49 | 55 | 22.2 | 78.5 |
| 28 | diphenyl sulfide | 0.52 | 65 | 17.4 | 77.1 |
| 29 | diphenyl disulfide | 0.49 | 65 | 21.0 | 77.7 |
| 30 | diphenyl sulfone | 0.48 | 60 | 18.7 | 73.9 |
| 31 | methylthiocyanate | 0.54 | 50 | 20.4 | 77.3 |
| 32 | carbon disulfide | 0.83 | 50 | 17.2 | 78.6 |
| 33 | dimethyl disulfide | 0.58 | 60 | 18.3 | 71.1 |
| 34 | dimethyl sulfone | 0.49 | 70 | 19.2 | 70.2 |
| 35 | L-thioproline | 0.50 | 90 | 22.0 | 74.8 |

EXAMPLE 36

In this example, the oxidation was conducted in the same manner as in the example 8 except using anhy- Results are shown in the Table IV.

TABLE IV

| Example No. | Inorganic sulfur compound | (m mol) | Reaction Time (min.) | Conversion of cyclohexanone [%] | Selectivity of adipaldehydic acid [%] |
|---|---|---|---|---|---|
| 38 | hydrogen sulfide | 1.00 | 60 | 25.7 | 80.2 |
| 39 | sodium hydrogensulfide | 0.50 | 110 | 23.7 | 75.8 |

TABLE IV-continued

| Example No. | Inorganic sulfur compound | (m mol) | Reaction Time (min.) | Conversion of cyclohexanone [%] | Selectivity of adipaldehydic acid [%] |
|---|---|---|---|---|---|
| 40 | sodium thiosulfate | 0.49 | 110 | 24.2 | 74.6 |
| 41 | sodium dithionite | 0.49 | 115 | 16.7 | 77.2 |
| 42 | sodium disulfite | 0.49 | 95 | 18.2 | 77.0 |

EXAMPLE 43 TO 49

In these examples, the oxidation was conducted in the same manner and reaction conditions as in the example 8 to 26 except using the organic nitrogen compounds in the Table V.

Results are shown in the Table V.

TABLE V

| Example No. | Organic nitrogen compound | (m mol) | Reaction Time (min.) | Conversion of cyclohexanone [%] | Selectivity of adipaldehydic acid [%] |
|---|---|---|---|---|---|
| 43 | pyridine | 0.65 | 60 | 31.9 | 73.8 |
| 44 | triethylamine | 0.49 | 55 | 32.7 | 73.6 |
| 45 | dimethylformamide | 0.60 | 65 | 32.0 | 70.9 |
| 46 | dimethylglyoxime | 0.50 | 125 | 32.2 | 80.2 |
| 47 | acetohydroxamic acid | 0.48 | 75 | 30.3 | 76.3 |
| 48 | 1,4-diazabicyclo [2,2,2] octane | 0.51 | 75 | 31.0 | 73.8 |
| 49 | urea | 0.50 | 60 | 34.8 | 72.4 |

EXAMPLES 50 TO 52

(Comparative examples)

In these examples, the oxidation was conducted in the same manner as in the Example 8 to 26 except using 1.02 m mol of copper chloride (CuCl$_2$) instead of ferric chloride and the sulfur compounds in the Table VI.

The result was shown in the Table VI.

TABLE VI

| Example No. | Sulfur compound | (m mol) | Reaction Time (min.) | Conversion of cyclohexanone [%] | Selectivity of adipaldehydic acid [%] |
|---|---|---|---|---|---|
| 50 | — | — | 315 | 17.1 | 50.2 |
| 51 | thiourea | 0.49 | 280 | 8.5 | 78.4 |
| 52 | 2-mercaptopyridine | 0.49 | 300 | 0 | 0 |

We claim:

1. A process for the synthesis of an oxocarboxylic acid of the formula (II):

RCO(CH$_2$)$_4$COOH   (II)

which comprises:

oxidizing a cyclohexanone of the formula (I):

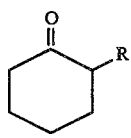

wherein R in both formulas has the same meaning and is hydrogen or alkyl, with molecular oxygen in the presence of (a) from 0.05 to 1000 parts by weight water, based on one part by weight cyclohexanone, and (b) an iron or iridium compound being soluble in the reaction system, said oxidation occurring at a temperature of from 0° to 200° C.

2. The process according to claim 1, wherein the oxidation reaction system further comprises a sulfur compound or an organic nitrogen compound.

3. The process according to claim 1, wherein the iron or iridium compound is present in an amount ranging from 0.1 to 100% by mole (as iron or iridium) of cyclohexanone.

4. The process according to claim 2, wherein the sulfur compound is present in an amount ranging from 0.1 to 100% by mole (as sulfur) of iron or iridium.

5. The process according to claim 2, wherein the organic nitrogen compound is present in an amount ranging from 0.1 to 600% by mole (as nitrogen) of iron or iridium.

6. The process according to claim 1, wherein the iron or iridium compound is a salt of an inorganic acid.

7. The process according to claim 6, wherein the iron compound is iron chloride or nitrate.

8. The process according to claim 2, wherein the sulfur compound is an iron or iridium saturated or unsaturated heterocyclic sulfur compound or an inorganc sulfur compound.

9. The process according to claim 2, wherein the organic nitrogen compound is an amine.

10. The process according to claim 2, wherein the organic nitrogen compound is pyridine.

11. The process according to claim 2, wherein an iron salt of an inorganic acid is combined with thiourea in the oxidation reaction medium.

12. The process according to claim 1, wherein iron chloride or nitrate is combined with thiourea in the oxidation reaction medium.

13. The process according to claim 1, wherein said cyclohexanone is cyclohexanone.

14. The process according to claim 1, wherein the reaction is a one-pass reaction in which the conversion of cyclohexanone reactant is controlled to less than 50%.

15. The process according to claim 1, wherein cyclohexanone is oxidized in the presence of iron chloride and thiourea.

16. The process according to claim 3, wherein the amount of iron or iridium compound ranges from 1 to 30 mole percent.

17. The process according to claim 2, wherein the sulfur compound is a compound of the formula: R—SH, R—S—R', R—S—S—R',

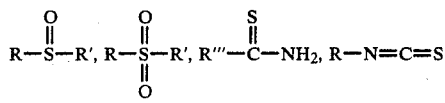

-continued

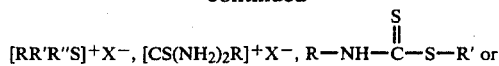, 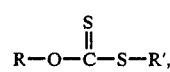

$$R-O-\overset{\overset{S}{\|}}{C}-S-R',$$

wherein R, R' and R" are alkyl or aryl; R''' is alkyl, aryl or amino, said alkyl groups having 1–20 carbon atoms and said aryl groups having 6–20 carbon atoms; and $X^-$ is an anion.

18. The process according to claim 17, wherein the sulfur compound is thiourea.

19. The process according to claim 2, wherein the organic nitrogen compound is an oxime.

20. The process according to claim 2, wherein the organic nitrogen compound is a hydroxamic acid.

21. The process according to claim 2, wherein the organic nitrogen compound is an amide.

* * * * *